(12) United States Patent
Kottenstette

(10) Patent No.: US 10,709,510 B2
(45) Date of Patent: Jul. 14, 2020

(54) SYSTEM AND METHOD FOR CONTROLLING A MOTOR IN A CATHETER PROCEDURE SYSTEM

(71) Applicant: Corindus, Inc., Waltham, MA (US)

(72) Inventor: Nicholas Kottenstette, Worcester, MA (US)

(73) Assignee: CORINDUS, INC., Waltham, MA (US)

( * ) Notice: Subject to any disclaimer, the term of this patent is extended or adjusted under 35 U.S.C. 154(b) by 928 days.

(21) Appl. No.: 15/105,377

(22) PCT Filed: Dec. 16, 2014

(86) PCT No.: PCT/US2014/070529
§ 371 (c)(1),
(2) Date: Jun. 16, 2016

(87) PCT Pub. No.: WO2015/095149
PCT Pub. Date: Jun. 25, 2015

(65) Prior Publication Data
US 2016/0310222 A1    Oct. 27, 2016

Related U.S. Application Data

(60) Provisional application No. 61/916,900, filed on Dec. 17, 2013.

(51) Int. Cl.
*A61B 34/30* (2016.01)
*H02P 21/18* (2016.01)
(Continued)

(52) U.S. Cl.
CPC ........ *A61B 34/30* (2016.02); *A61B 17/00234* (2013.01); *A61B 90/06* (2016.02);
(Continued)

(58) Field of Classification Search
CPC ........ A61B 90/00; A61B 34/00; A61M 25/00; H02P 21/18; H02P 4/00; H02P 8/00; H02P 7/00; H02P 21/20
See application file for complete search history.

(56) References Cited

U.S. PATENT DOCUMENTS 5,317,246 A     5/1994   Wei
5,936,369 A *   8/1999   Iwashita ............. G05B 19/19
                                                   318/609
(Continued)

OTHER PUBLICATIONS

International Search Report and Written Opinion for PCT/US2014/070529; dated Mar. 10, 2015; 8 pages.
(Continued)

*Primary Examiner* — Bickey Dhakal
*Assistant Examiner* — Said Bouziane
(74) *Attorney, Agent, or Firm* — Rathe Lindenbaum LLP

(57) ABSTRACT

A catheter procedure system includes a bedside system having a percutaneous device, at least one drive mechanism coupled to the percutaneous device and at least one motor coupled to the at least one drive mechanism. The system also includes a workstation that is coupled to the bedside system and includes a user interface and a controller coupled to the bedside system and the user interface. The controller is programmed to receive at last one parameter of the motor, determine a quadrature current of the motor based on at least the at least one parameter, determine a load torque on the motor based on at least the quadrature current, an angular velocity and an angular acceleration and control the operation of the motor based on the load torque, wherein the operation of the motor causes the drive mechanism to move the percutaneous device.

24 Claims, 8 Drawing Sheets

(51) Int. Cl.
    *H02P 21/20*     (2016.01)
    *H02P 8/00*     (2006.01)
    *A61B 90/00*     (2016.01)
    *A61B 17/00*     (2006.01)
    *A61M 25/01*     (2006.01)
    *H02P 8/20*     (2006.01)

(52) U.S. Cl.
    CPC ........... *A61M 25/0113* (2013.01); *H02P 8/00* (2013.01); *H02P 8/20* (2013.01); *H02P 21/18* (2016.02); *H02P 21/20* (2016.02); *A61B 2017/00044* (2013.01); *A61B 2017/00477* (2013.01); *A61B 2034/301* (2016.02); *A61B 2090/066* (2016.02)

(56) References Cited

U.S. PATENT DOCUMENTS

| | | | |
|---|---|---|---|
| 6,158,553 | A | 12/2000 | Oshima et al. |
| 6,262,550 | B1 | 7/2001 | Kliman et al. |
| 6,396,234 | B1* | 5/2002 | Tateishi ................. G05B 5/01 318/610 |
| 7,203,601 | B2* | 4/2007 | Ito .......................... B25J 9/1687 702/33 |
| 7,541,759 | B2* | 6/2009 | Hirai .................... H02H 7/0851 318/272 |
| 7,627,440 | B2* | 12/2009 | Rehm .................. G05B 19/416 318/563 |
| 7,963,288 | B2 | 6/2011 | Rosenberg et al. |
| 2006/0012321 | A1* | 1/2006 | Rozman .................. F02C 7/275 318/432 |
| 2006/0179859 | A1* | 8/2006 | Nakata ..................... H02P 6/06 62/228.1 |
| 2012/0130400 | A1* | 5/2012 | Brock .................... A61B 34/71 606/130 |
| 2013/0012930 | A1 | 1/2013 | Morales et al. |
| 2013/0231678 | A1 | 9/2013 | Wenderow et al. |
| 2014/0285124 | A1* | 9/2014 | Derammelaere ....... H02P 23/14 318/400.02 |

OTHER PUBLICATIONS

Extended European Search Report for EP 14872216.8; dated Jul. 25, 2017; 11 pages.

\* cited by examiner

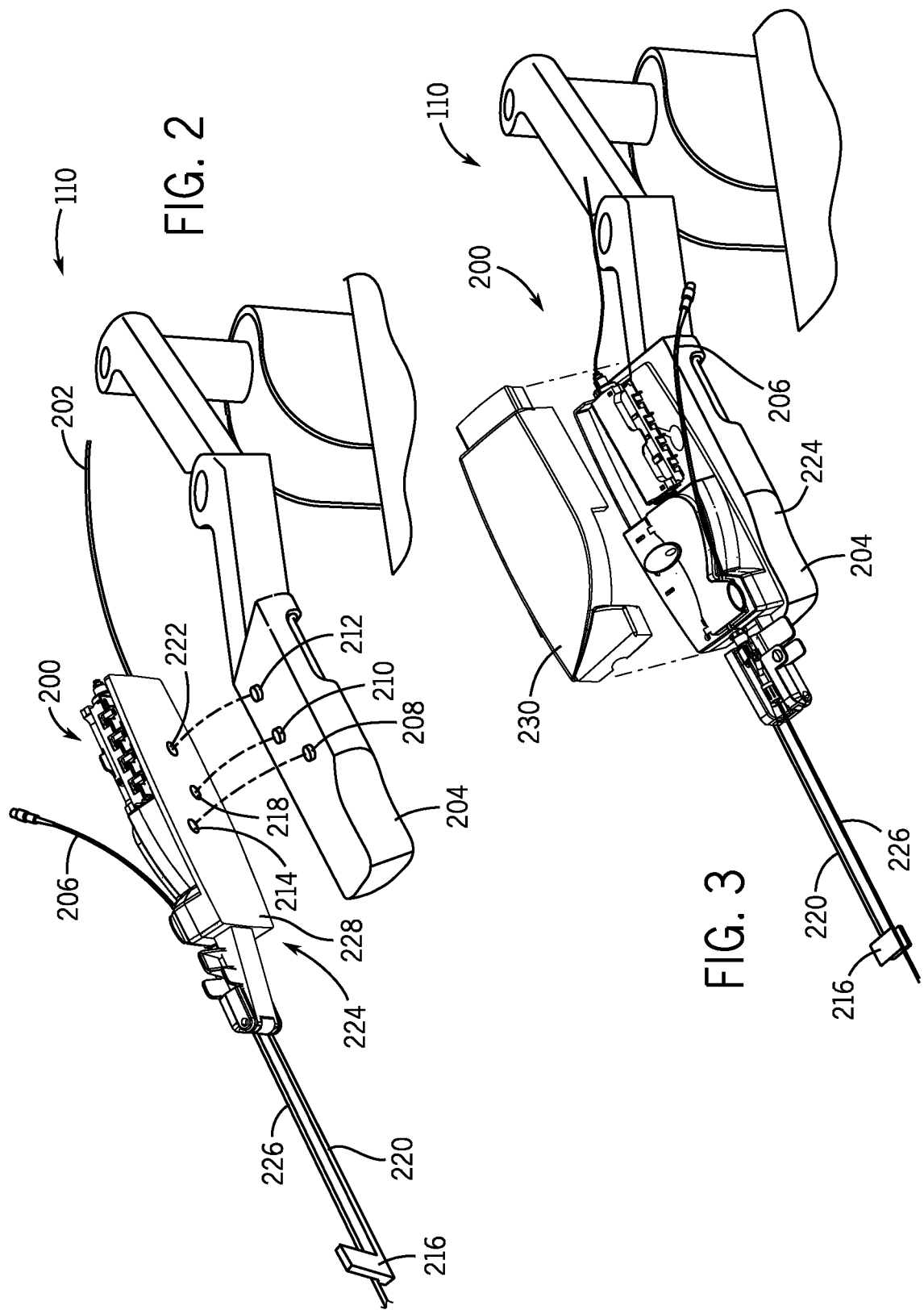

SYSTEM AND METHOD FOR CONTROLLING A MOTOR IN A CATHETER PROCEDURE SYSTEM

CROSS REFERENCE TO RELATED APPLICATIONS

The present application claims the benefit of U.S. Provisional Application No. 61/916,900, filed Dec. 17, 2013, entitled "TORQUE SENSOR USING BLDC AND STEPPER MOTORS", herein incorporated by reference in its entirety.

FIELD OF THE INVENTION

The present invention relates generally to the field of robotic catheter systems for performing diagnostic and/or therapeutic procedures and in particular, to a system and method for controlling a motor used to drive portions of the catheter system that includes determining a load torque using the motor.

BACKGROUND OF THE INVENTION

Catheters may be used for many medical procedures, including inserting a guide wire, delivering a stent and delivering and inflating a balloon. Catheterization procedures are commonly performed for diagnosis and treatment of diseases of the heart and vascular systems. The catheterization procedure is generally initiated by inserting a guide wire into a blood vessel in the patient's body. The guide wire is then guided to the desired location, most commonly in one of the heart vessels or elsewhere in the vascular system. At this point, the catheter is slid over the guide wire into the blood vessel and/or heart. Once the catheter is in the desired position, the guide wire can then be removed leaving the catheter in location. Alternatively, in some procedures, the catheter is inserted without using a guide wire. The catheter may be used to pass ancillary devices into the body such as an angioplasty balloon, or to perform other diagnostic or therapeutic procedures.

For manual insertion of a catheter, the physician applies torque and axial push force on the proximal end of a guide wire to effect tip direction and axial advancement at the distal end. Robotic catheter system have been developed that may be used to aid a physician in performing a catheterization procedure such as a percutaneous coronary intervention (PCI). The physician uses a robotic catheter system to precisely steer a coronary guide wire and balloon/stent device in order to, for example, widen an obstructed artery. The physician relies on position feedback signals provided by both the robotic catheter system and a fluoroscopic imaging system in order to complete the procedure Robotic catheter systems, however, do not provide the force feedback the physician experiences when manually performing PCI. In order to provide force sensing capabilities, an appropriately selected load cell or rotary torque sensor could be used; however, these are costly devices which can drastically increase the required work space volume to perform the PCI procedure.

It would be desirable to provide a system and method for controlling a motor used to drive portions of the catheter system including sensing torque using the motor. In various embodiments, either a brushless DC (BLDC) motor or a stepper motor may be used to determine the load torque being exerted on the motor. Presenting the real time force and torque required to drive a coronary device in the patient may enhance the performance of the robotic catheter system.

BRIEF DESCRIPTION OF THE INVENTION

In accordance with an embodiment, a catheter procedure system includes a bedside system comprising a percutaneous device, at least one drive mechanism coupled to the percutaneous device and at least one motor coupled to the at least one drive mechanism; and a workstation coupled to the bedside system including a user interface and a controller coupled to the bedside system and the user interface, the controller programmed to receive at last one parameter of the motor, determine a quadrature current of the motor based on at least the at least one parameter, determine a load torque on the motor based on at least the quadrature current, an angular velocity and an angular acceleration and control the operation of the motor based on the load torque, wherein the operation of the motor causes the drive mechanism to move the percutaneous device.

In accordance with another embodiment, a method for controlling a motor in a catheter procedure system includes receiving at least one parameter of the motor, determining a quadrature current of the motor based on at least the at least one parameter, determining a load torque on the motor based on at least the quadrature current, an angular velocity and an angular acceleration and controlling the operation of the motor based on the load torque, wherein the operation of the motor causes the drive mechanism to move the percutaneous device.

BRIEF DESCRIPTION OF THE DRAWINGS

The invention will become more fully understood from the following detailed description, taken in conjunction with the accompanying drawings, wherein the reference numerals refer to like parts in which:

FIG. 2 is a perspective view of a bedside system in accordance with an embodiment;

FIG. 3 is a perspective view of a bedside system in accordance with an embodiment;

DETAILED DESCRIPTION

Figure 1:
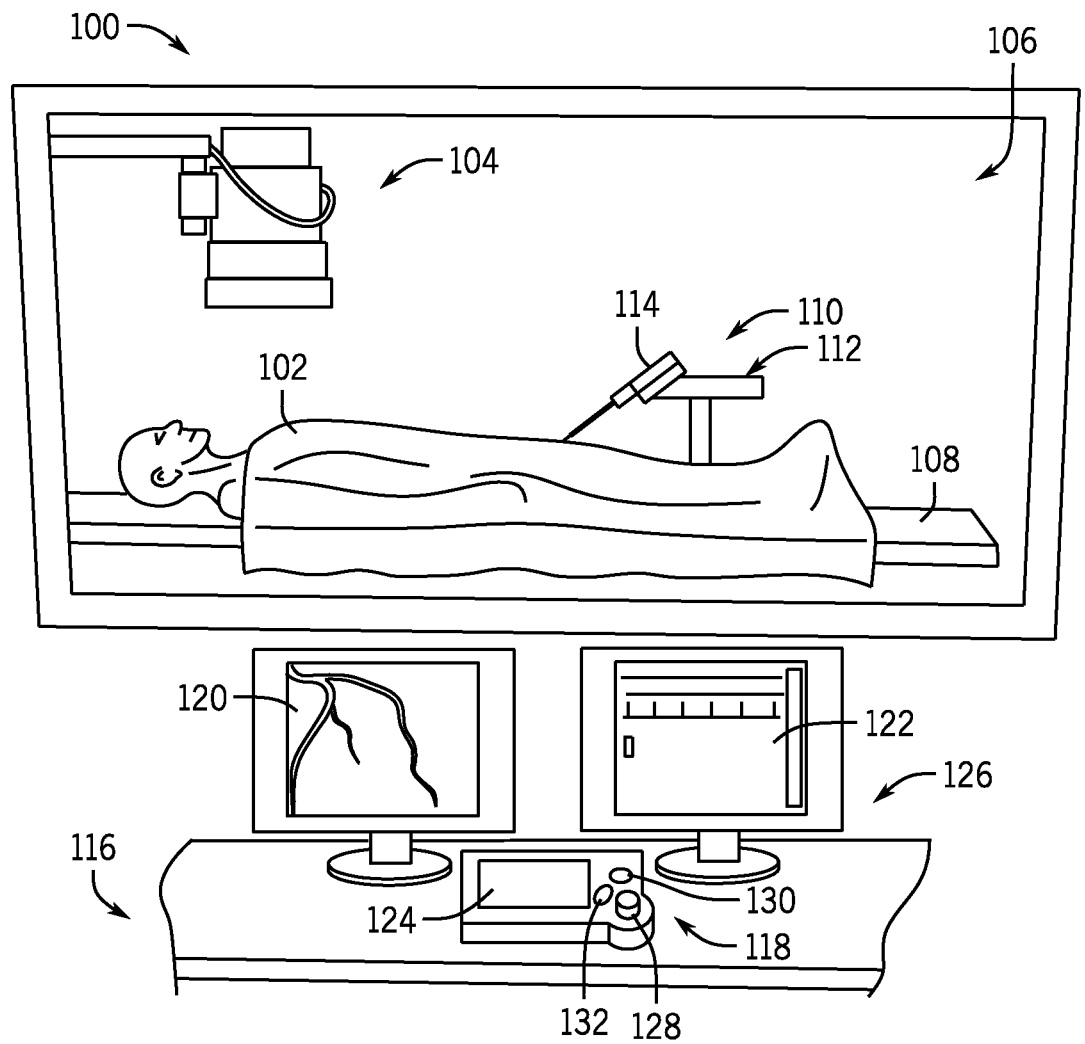
FIG. 1 is a perspective view of an exemplary catheter procedure system in accordance with an embodiment.

FIG. 1 is a perspective view of an exemplary catheter procedure system in accordance with an embodiment. In FIG. 1, a catheter procedure system 100 may be used to perform catheter based medical procedures (e.g., a percutaneous intervention procedure). Percutaneous intervention procedures may include diagnostic catheterization procedures during which one or more catheters are used to aid in the diagnosis of a patient's disease. For example, during one embodiment of a catheter based diagnostic procedure, a contrast media is injected onto one or more coronary arteries through a catheter and an image of the patient's heart is taken. Percutaneous intervention procedures may also include catheter based therapeutic procedures (e.g., angioplasty, stent placement, treatment of peripheral vascular disease, etc.) during which a catheter is used to treat a disease. It should be noted, however, that one skilled in the art would recognize that certain specific percutaneous intervention devices or components (e.g., type of guide wire, type of catheter, etc.) will be selected based on the type of procedure that is to be performed. Catheter procedure system 100 is capable of performing any number of catheter based medical procedures with minor adjustments to accommodate the specific percutaneous intervention devices to be used in the procedure. In particular, while the embodiments of catheter procedure system 100 describe herein are explained primarily in relation to the diagnosis and/or treatment of coronary disease, catheter procedure system 100 may be used to diagnose and/or treat any type of disease or condition amenable to diagnosis and/or treatment via a catheter based procedure.

Catheter procedure system 100 includes lab unit 106 and workstation 116. Catheter procedure system 100 includes a robotic catheter system, shown as bedside system 110, located within lab unit 106 adjacent a patient 102. Patient 102 is supported on a table 108. Generally, bedside system 110 may be equipped with the appropriate percutaneous intervention devices or other components (e.g., guide wires, guide catheters, working catheters, catheter balloons, stents, contrast media, medicine, diagnostic catheters, etc.) to allow the user to perform a catheter based medical procedure via a robotic system by operating various controls such as the controls located at workstation 116. Bedside system 110 may include any number and/or combination of components to provide bedside system 110 with the functionality described herein. Bedside system 110 includes, among other elements, a cassette 114 supported by a robotic arm 112 which is used to automatically feed a guide wire into a guide catheter seated in an artery of the patient 102.

Bedside system 110 is in communication with workstation 116, allowing signals generated by the user inputs of workstation 116 to be transmitted to bedside system 110 to control the various functions of bedside system 110. Bedside system 110 may also provide feedback signals (e.g., operating conditions, warning signals, error codes, etc.) to workstation 116. Bedside system 110 may be connected to workstation 116 via a communication link 140 (shown in FIG. 4) that may be a wireless connection, cable connections, or any other means capable of allowing communication to occur between workstation 116 and bedside system 110.

Workstation 116 includes a user interface 126 configured to receive user inputs to operate various components or systems of catheter procedure system 100. User interface 126 includes controls 118 that allow the user to control bedside system 110 to perform a catheter based medical procedure. For example, controls 118 may be configured to cause bedside system 110 to perform various tasks using the various percutaneous intervention devices with which bedside system 110 may be equipped (e.g., to advance, retract, or rotate a guide wire, advance, retract or rotate a working catheter, advance, retract, or rotate a guide catheter, inflate or deflate a balloon located on a catheter, position and/or deploy a stent, inject contrast media into a catheter, inject medicine into a catheter, or to perform any other function that may be performed as part of a catheter based medical procedure). Cassette 22 includes various drive mechanisms to cause movement (e.g., axial and rotational movement) of the components of the bedside system 110 including the percutaneous intervention devices.

In one embodiment, controls 118 include a touch screen 124, one or more joysticks 128 and buttons 130, 132. The joystick 128 may be configured to advance, retract, or rotate various components and percutaneous intervention devices such as, for example, a guide wire, a guide catheter or a working catheter. Buttons 130, 132 may include, for example, an emergency stop button and a multiplier button. When an emergency stop button is pushed a relay is triggered to cut the power supply to bedside system 110. Multiplier button acts to increase or decrease the speed at which the associated component is moved in response to a manipulation of controls 118. In one embodiment, controls 118 may include one or more controls or icons (not shown) displayed on touch screen 124, that, when activated, causes operation of a component of the catheter procedure system 100. Controls 118 may also include a balloon or stent control that is configured to inflate or deflate a balloon and/or a stent. Each of the controls may include one or more buttons, joysticks, touch screen, etc. that may be desirable to control the particular component to which the control is dedicated. In addition, touch screen 124 may display one or more icons (not shown) related to various portions of controls 118 or to various components of catheter procedure system 100.

User interface 126 may include a first monitor or display 120 and a second monitor or display 122. First monitor 120 and second monitor 122 may be configured to display information or patient specific data to the user located at workstation 116. For example, first monitor 120 and second monitor 122 may be configured to display image data (e.g., x-ray images, MRI images, CT images, ultrasound images, etc.), hemodynamic data (e.g., blood pressure, heart rate, etc.), patient record information (e.g., medical history, age, weight, etc.). In addition, first monitor 120 and second monitor 122 may be configured to display procedure specific information (e.g., duration of procedure, catheter or guide wire position, volume of medicine or contrast agent delivered, etc.). Monitor 120 and monitor 122 may be configured to display information regarding the position the guide catheter. Further, monitor 120 and monitor 122 may be configured to display information to provide the functionalities associated with controller 134 (shown in FIG. 4) discussed below. In another embodiment, user interface 126 includes a single screen of sufficient size to display one or more of the display components and/or touch screen components discussed herein.

Catheter procedure system 100 also includes an imaging system 104 located within lab unit 106. Imaging system 104 may be any medical imaging system that may be used in conjunction with a catheter based medical procedure (e.g., non-digital x-ray, digital x-ray, CT, MRI, ultrasound, etc.). In an exemplary embodiment, imaging system 104 is a digital x-ray imaging device that is in communication with workstation 116. In one embodiment, imaging system 104 may include a C-arm (not shown) that allows imaging system 104 to partially or completely rotate around patient 102 in order to obtain images at different angular positions relative to patient 102 (e.g., sagittal views, caudal views, anterior-posterior views, etc.).

Imaging system 104 may be configured to take x-ray images of the appropriate area of patient 102 during a particular procedure. For example, imaging system 104 may be configured to take one or more x-ray images of the heart to diagnose a heart condition. Imaging system 104 may also be configured to take one or more x-ray images during a catheter based medical procedure (e.g., real time images) to assist the user of workstation 116 to properly position a guide wire, guide catheter, stent, etc. during the procedure. The image or images may be displayed on first monitor 120 and/or second monitor 122. In particular, images may be displayed on first monitor 120 and/or second monitor 122 to allow the user to, for example, accurately move a guide catheter into the proper position.

In addition, a user of workstation 116 may be able to control the angular position of imaging system 104 relative to the patient to obtain and display various views of the patient's heart on first monitor 120 and/or second monitor 122. Displaying different views at different portions of the procedure may aid the user of workstation 116 to properly move and position the percutaneous intervention devices within the 3D geometry of the patient's heart. In an embodiment, imaging system 104 may be any 3D imaging modality such as an x-ray based computed tomography (CT) imaging device, a magnetic resonance imaging device, a 3D ultrasound imaging device, etc. In this embodiment, the image of the patient's heart that is displayed during the procedure may be a 3D image. In addition, controls 118 may also be configured to allow the user positioned at workstation 116 to control various functions of imaging system 104 (e.g., image capture, magnification, collimation, c-arm positioning, etc.).

Referring now to FIGS. 2 and 3, an exemplary embodiment of a cassette for use with a robotic catheter system is shown. Cassette 200 may be equipped with a guide wire 202 and a working catheter 206 to allow a user to perform a catheterization procedure utilizing cassette 200. In this embodiment, bedside system 110 includes a cassette 200 configured to be mounted to a motor drive base 204. FIG. 2 shows a bottom perspective view of cassette 200 prior to mounting to motor drive base 204. Motor drive base 204 includes a first capstan 208, a second capstan 210, and a third capstan 212, and cassette 200 includes a first capstan socket 214, a second capstan socket 218, and a third capstan socket 222. Cassette 200 includes a housing 224, and housing 224 includes a base plate 228.

Each of the capstan sockets 214, 218, 222 is configured to receive one of the capstans 208, 210, 212 of motor drive base 204. In the embodiment shown, base plate 228 includes a hole or aperture aligned with each of the capstan sockets 214, 218, and 222 to allow each capstan to engage with the appropriate capstan socket. The engagement between the capstans and capstan sockets allows the transfer of energy (e.g., rotational movement) generated by one or more actuators (e.g., motors) located within motor drive base 204 to each of the drive mechanisms (e.g., axial and rotational drive mechanisms) within cassette 200. Capstans and capstan sockets are one embodiment of a motor coupler that may be used to couple the motors to the axial and rotational drive mechanisms in the cassette 200. Other motor couplers that can couple the motor to the motors to the drive mechanisms are also contemplated.

In one embodiment, a single actuator provides energy to each of the drive mechanisms. In another embodiment, there is an actuator that drives capstan 208, an actuator that drives capstan 210 and an actuator that drives capstan 212. Further, the positioning of the capstans and capstan sockets helps the user to align cassette 200 relative to motor drive base 204 by allowing cassette 200 to be mounted to motor drive base 204 only when all three capstan sockets are aligned with the proper capstan.

In one embodiment, the motors that drive capstans 208, 210, and 212 are located within motor drive base 204. In another embodiment, the motors that drive capstans 208, 210, and 210 may be located outside of base 204 and connected to cassette 200 via an appropriate transmission device (e.g., shaft, cable, other mechanical coupler, etc.). In yet another embodiment, cassette 200 includes motors located within the housing of cassette 200. In another embodiment, cassette 200 does not include capstan sockets 214, 218 and 222, but includes an alternative mechanism for transferring energy (e.g., rotational motion) from an actuator external to the cassette to each of the cassette drive mechanisms. For example, rotational movement may be transferred to the drive mechanisms of cassette 200 via alternating or rotating magnets or magnetic fields located within motor drive base 204.

In the embodiment, shown, cassette 200 also includes a guide catheter support 216 that supports guide catheter 226 at a position spaced from cassette 200. As shown, guide catheter support 216 is attached to cassette 200 by a rod 220. Rod 220 and guide catheter support 216 are strong enough to support guide catheter 226 without buckling. Guide catheter support 216 supports guide catheter 226 at a position spaced apart from the cassette, between the patient and the cassette to prevent buckling, bending, etc. of the portion of guide catheter 226 between the cassette and the patient.

Referring to FIG. 3, cassette 200 is shown mounted to motor drive base 204. As shown in FIG. 3, cassette 200 includes an outer cassette cover 230 that may be attached to housing 224. When attached to housing 224, outer cassette cover 230 is positioned over and covers each of the drive mechanisms of cassette 200. By covering the drive assemblies of cassette 200, outer cassette cover 230 acts to prevent accidental contact with the drive mechanisms of cassette 200 while in use.

Figure 4:
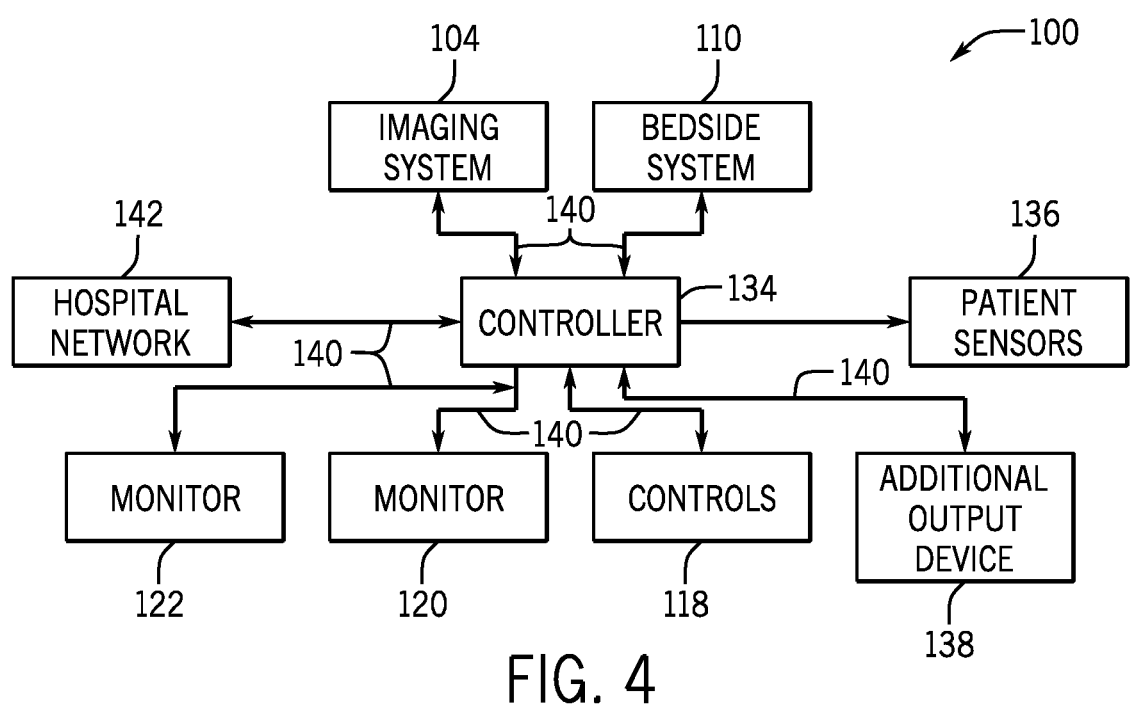
FIG. 4 is a schematic block diagram of a catheter procedure system in accordance with an embodiment.

Referring to FIG. 4, a block diagram of catheter procedure system 100 is shown according to an exemplary embodiment. Catheter procedure system 100 may include a control system, shown as controller 134. Controller 134 may be part of workstation 116. Controller 134 may generally be an electronic control unit suitable to provide catheter procedure system 100 with the various functionalities described herein. For example, controller 134 may be an embedded system, a dedicated circuit, a general purpose system programmed with the functionality described herein, etc. Controller 134 is in communication with one or more bedside systems 110, controls 118, monitors 120 and 122, imaging system 104 and patient sensors 35 (e.g., electrocardiogram ("ECG") devices, electroencephalogram ("EEG") devices, blood pressure monitors, temperature monitors, heart rate monitors, respiratory monitors, etc.). In various embodiments, controller 134 is configured to generate control signals based on the user's interaction with controls 118 and/or based upon information accessible to controller 134 such that a medical procedure may be performed using catheter procedure system 100. In addition, controller 134 may be in communication with a hospital data management system or hospital network 142 and one or more additional output devices 138 (e.g., printer, disk drive, cd/dvd writer, etc.).

Communication between the various components of catheter procedure system 100 may be accomplished via communication links 140. Communication links 140 may be dedicated wires or wireless connections. Communication links 140 may also represent communication over a network. Catheter procedure system 100 may be connected or configured to include any other systems and/or devices not explicitly shown. For example, catheter procedure system 100 may include IVUS systems, image processing engines, data storage and archive systems, automatic balloon and/or stent inflation systems, medicine injection systems, medicine tracking and/or logging systems, user logs, encryption systems, systems to restrict access or use of catheter procedure system 100, etc.

Figure 5:
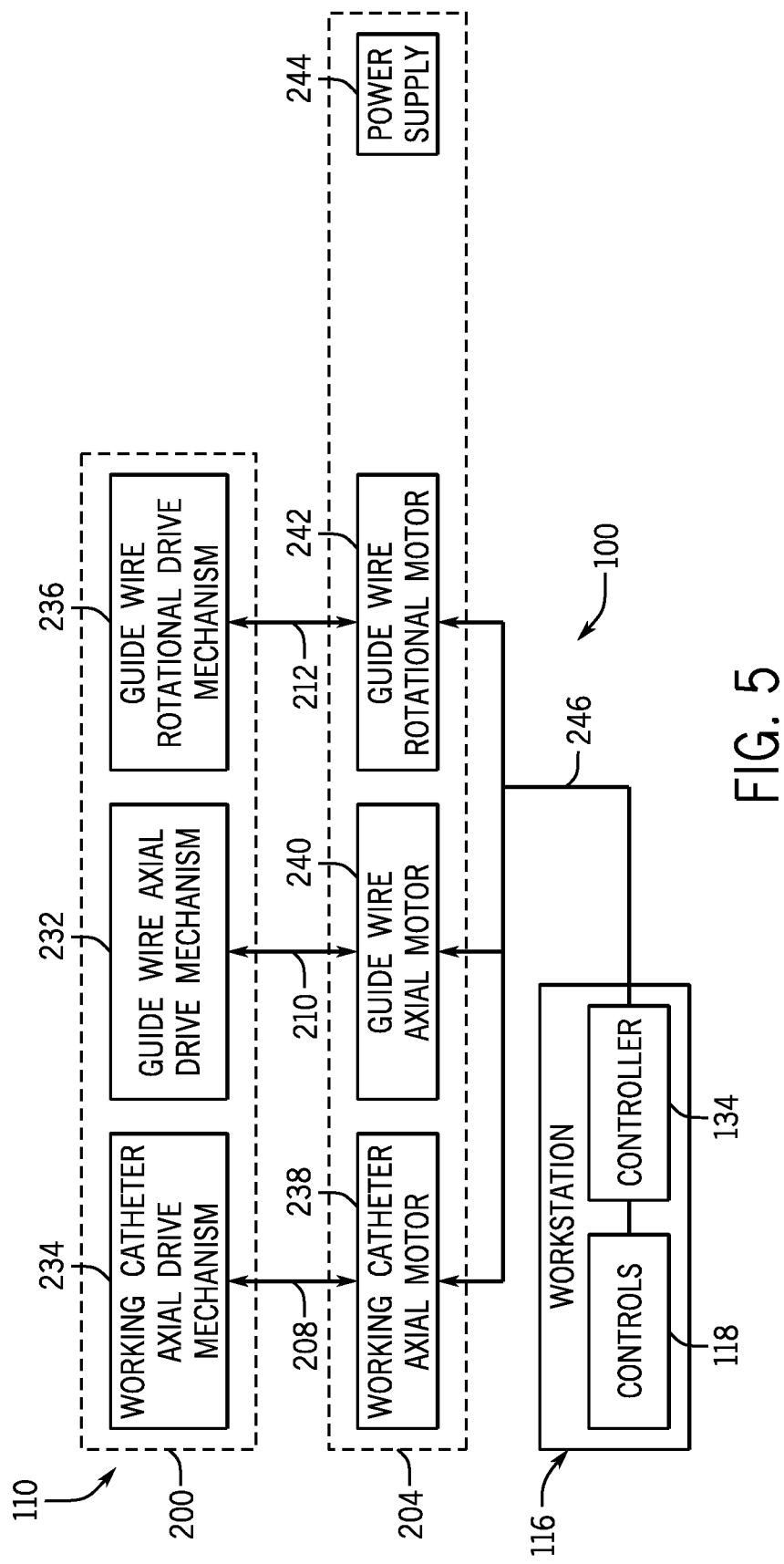
FIG. 5 is a block diagram of a catheter procedure system showing motors located within a motor drive base in accordance with an embodiment.

As mentioned, controller 134 is in communication with bedside system 110 and may provide control signals to the bedside system 110 to control the operation of the motors and drive mechanisms used to drive the percutaneous intervention devices (e.g., guide wire, catheter, etc.). FIG. 5 is a block diagram of a catheter procedure system showing motors located within a motor drive based in accordance with an embodiment. Cassette 200 includes a guide wire axial drive mechanism 232 that provides for advancement and/or retraction of guide wire 202. A working catheter axial drive mechanism 234 provides for advancement and/or retraction of working catheter 206. Cassette 200 also includes a guide wire rotational drive mechanism 236 that is configured to cause guide wire 202 to rotate about its longitudinal axis.

Motor drive base 204 includes working catheter axial drive motor 238, guide wire axial drive motor 240, a guide wire rotational drive motor 242, and a power supply 244. Working catheter axial drive motor 238 drives capstan 208, guide wire axial drive motor 240 drives capstan 210 and guide wire rotational drive motor 242 drives capstan 212 to cause movement of working catheter 206 and guide wire 202. Motors 238, 240, and 242 are in communication with controller 143 such that control signals 246 may be received by motors 238, 240 and 242. Motors 238, 240 and 242 respond to control signals 246 by varying the rotation of capstans 208, 210 and 212 thereby varying the movement of working catheter 206 and guide wire 202 caused by drive mechanisms 232, 234 and 236. As shown, motor drive base 204 also includes a power supply 244 that may be, for example, a battery, the AC building supply, etc.

In various embodiments, the motors may be a permanent magnet synchronous motor (PMSM) such as a brushless DC (BLDC) or a stepper motor. Controller 134 is configured to receive data from a motor (e.g., motors 238, 240, 242). As mentioned, controller 134 also provides control signals 246 to a motor to control the operation of the motor. Each motor used to drive the various devices in the catheter procedure system 100 may be used in conjunction with controller 134 as a torque sensor to determine the load torque on the motor in order to, for example, provide feedback to the user and to control the operation of the motor to advance, retract and rotate a device. Accordingly, a separate torque sensor is not required to sense the load torque on a motor in the catheter procedure system. While the following discusses a method for sensing torque in relation to a motor used in a catheter procedure system, it should be understood that the methods described herein may be used in other systems using a motor to drive a device.

Figure 6:
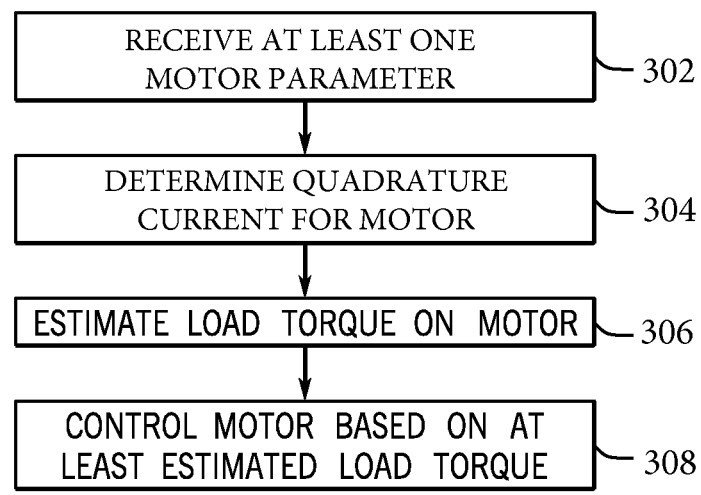
FIG. 6 illustrates a method for controlling a motor including determining a load torque using the motor in accordance with an embodiment.

FIG. 6 illustrates a method for controlling a motor including determining a load torque using the motor in accordance with an embodiment. At block 302, at least one parameter of the motor is received by a controller (e.g., controller 134 shown in FIGS. 4 and 5). The motor parameter may be, for example, a motor angular position ($\theta_m$), a motor angular velocity ($\omega_m$), phase currents, voltages, etc. The motor angular position may be measured using, for example, a rotary encoder and the currents may be measures using, for example, either a current sense resistor or hall effect sensor with appropriate analog signal conditioning circuitry. In one embodiment, the angular position is converted to a filtered version ($\hat{\theta}_m$) based on the measured angular position ($\theta_m$) and a reference angular velocity ($\omega_r$). For example, the filtered version of the angular position ($\hat{\theta}_m$) may be determined by:

$$\hat{\theta}_m = y(k) + \theta_m \quad (1)$$

where y(k) is a discrete time integrator defined as:

$$y(k) = y(k-1) + \left(\frac{T_s}{2}\right) * (u(k) + (u(k-1)) \quad (2)$$

where $u(k) = \omega_m(k-1)$ and $\omega_r = \omega_m$.

Figure 7:
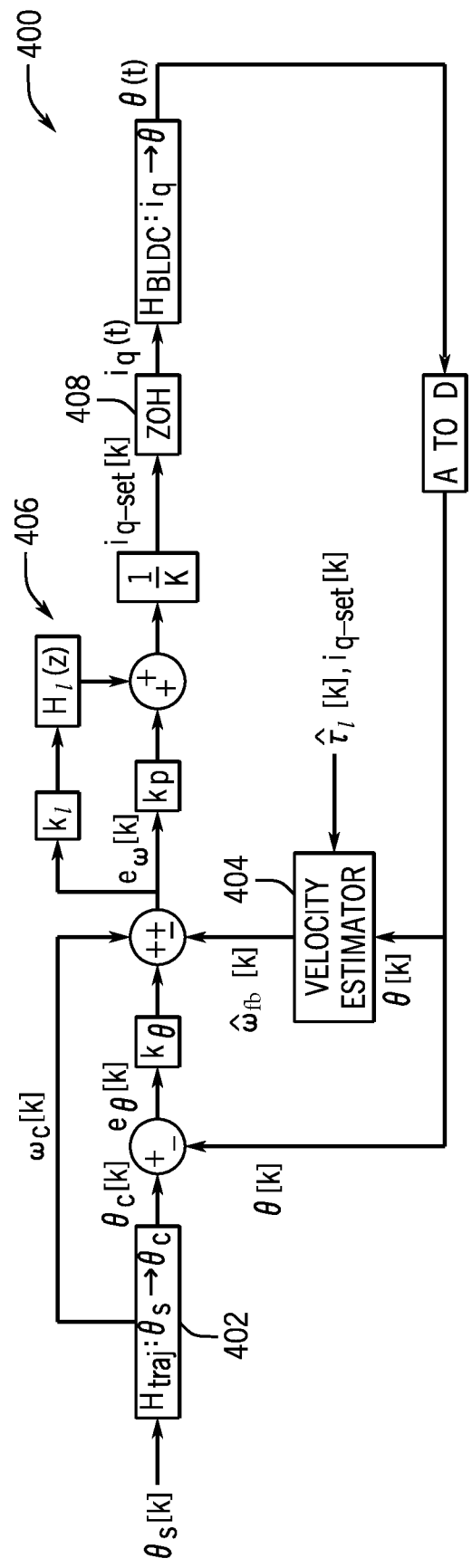
FIG. 7 illustrates a position control system in accordance with an embodiment.

At block 304, a quadrature current is determined. In an embodiment where the motor is a BLDC motor, the quadrature current (Q-current, $i_q$) is determined based on the filtered version of the measured motor angular position ($\hat{\theta}_m$), and a reference motor angular position ($\theta_r$). In another embodiment, the Q-current may be determined based on the measured motor angular position rather than the filtered version of the measured motor angular position. In another embodiment, a predetermined quadrature current setpoint may be used. By choosing to sense torque in a BLDC motor by directly controlling the quadrature current $i_q$, the torque is directly controlled with the motor. Therefore, a position control system (e.g., a motor position proportional integral (PI) controller) is required to maintain the position of the motor. The position control system is used to determine the Q-current and control the angular position and velocity of the BLDC motor. FIG. 7 illustrates an exemplary position control system in accordance with the embodiment. The position control system 400 includes two control loops. An inner control loop is used to maintain a desired velocity ($\omega_c(k)$) and an outer control loop is used to maintain a desired angular position ($\theta_c(k)$).

Figure 8:
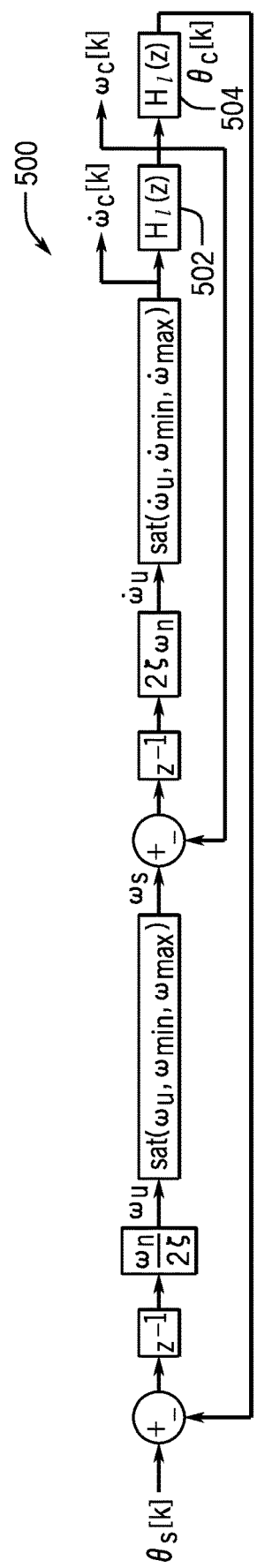
FIG. 8 illustrates a discrete time command filter in accordance with an embodiment.

A discrete time (DT) command filter 402 (denoted $H_{traj}$: $\theta_S \rightarrow \theta_C$) is used to generate a command position, angular velocity and angular acceleration for the BLDC motor. FIG. 8 illustrates an exemplary DT command filter in accordance with an embodiment. In order to ensure trajectory tracking, the DT command filter 500 depicted in FIG. 8 is implemented to generate a command setpoint $\theta_C[k]$ from a desired setpoint $\theta_S[k]$. The DT command filter 500 has a bandwidth $\omega_n > 0$ and limits the magnitude of a command angular velocity $\omega_c[k]$ and a command angular acceleration $\dot{\omega}_c$ so that $\omega_c \in [\omega_{min}, \omega_{max}]$ and $\dot{\omega}_c \in [\dot{\omega}_{min}, \dot{\omega}_{max}]$. FIG. 8 depicts two DT integrators 502, 504 which are denoted by the DT transfer function $$H_I(z) = \frac{Y_I(z)}{U_I(z)} = \frac{T_s}{2} \frac{z+1}{z-1} \quad (3)$$

where the DT relationship is given by:

$$y_I[k] = y_I[k-1] + \frac{T_s}{2}(u_I[k] + u_I[k-1]) \quad (4)$$

where $T_s$ is a sampling rate. In order to limit the range of the angular velocity command $\omega_c[k]$ and command angular acceleration $\dot{\omega}_c[k]$, a saturation function denoted sat ($u_s$, $u_{min}$, $u_{max}$) is used such that:

$$sat(u_s, u_{min}, u_{max}) = \begin{cases} u_{min} & \text{if } u_s < u_{min}, \\ u_s & \text{if } u_{min} \leq u_s \leq u_{max}, \\ u_{max} & \text{otherwise.} \end{cases} \quad (5)$$

The following equations summarize the implementation of the DT command filter 500 to generate the command position $\theta_C[k]$, angular velocity $\omega_c(k)$ and angular acceleration $\dot{\omega}_c(k)$ for the BLDC motor:

$$\omega_u[k] = \frac{\omega_n}{2\zeta}(\theta_s[k-1] - \theta_c[k-1]), \zeta \in (0, 1], \omega_n > 0 \quad (6)$$

$$\omega_s[k] = sat(\omega_u[k], \omega_{min}, \omega_{max}), \omega_{min}, \omega_{max} \in \mathbb{R} \quad (7)$$

$$\dot{\omega}_u[k] = 2\zeta\omega_n(\omega_s[k-1] - \omega_c[k-1]) \quad (8)$$

$$\dot{\omega}_c[k] = sat(\dot{\omega}_u[k], \dot{\omega}_{min}, \dot{\omega}_{max}), \dot{\omega}_{min}, \dot{\omega}_{max} \in \mathbb{R} \quad (9)$$

$$\omega_c[k] = \omega_c[k-1] + \frac{T_s}{2}(\dot{\omega}_c[k] + \dot{\omega}_c[k-1]) \quad (10)$$

$$\theta_c[k] = \theta_c[k-1] + \frac{T_s}{2}(\omega_c[k] + \omega_c[k-1]) \quad (11)$$

Returning to FIG. 7, a velocity estimator 404 is used to estimate the angular velocity $\hat{\omega}_{fb}[k]$. In one embodiment, the angular velocity $\hat{\omega}_{fb}[k]$ is estimated by differentiating the sampled angular position $\theta[k] = \theta(kT_S)$ of the rotor. In particular, the continuous time transfer function is estimated by:

$$H_d(s) = \frac{\hat{\omega}_{fb}(s)}{\theta(s)} = \frac{\omega_d s}{s + \omega_d} \text{ in which } 0 < \omega_d < \frac{\pi}{T_e} \quad (12)$$

with a DT filter $H_d(z)$. The DT filter $H_d(s)$ may be realized with a feedback loop containing an integrator in the feedback path and a gain of $\omega_d$ in the output path. $H_d(s)$ may be approximated by replacing the integrator with $H_I(z)$ and solving the DT equations which are:

$$E_d(z) = \theta(z) - \omega_d H_I(z) E_d(z) \quad (13)$$

$$\hat{\omega}_{fb}(z) = \omega_d E_d(z)$$

$$\frac{\hat{\omega}_{fb}(z)}{\theta(z)} = \frac{\omega_d}{1 + \omega_d H_I(z)}$$

$$\frac{\hat{\omega}_{fb}(z)}{\theta(z)} = \frac{\omega_d(z-1)}{\frac{2 + \omega_d T_s}{2}z + \frac{\omega_d T_s - 2}{2}}$$

$$\frac{\hat{\omega}_{fb}(z)}{\theta(z)} = \frac{2\omega_d}{2 + \omega_d T_s} \cdot \frac{z-1}{z + \frac{\omega_d T_s - 2}{2 + \omega_d T_s}};$$

Therefore:

$$\hat{\omega}_{fb}[k] = \frac{2 - \omega_d T_s}{2 + \omega_d T_s}\hat{\omega}_{fb}[k-1] + \frac{2\omega_d}{2 + \omega_d T_s}(\theta[k] - \theta[k-1]) \quad (14)$$

Feedback control 406 is used for closed loop velocity and position control of the BLDC motor. The most inner feedback loop ensures angular velocity tracking with both a proportional term $k_p e_\omega[k]$ ($k_p > 0$) and an integrator term (e.g., with anti-windup) which is denoted $H_I(z) k_I e_\omega(z)$ ($k_I > 0$, where $e_\omega(z)$ is the z-transform of $e_\omega[k]$). The outer feedback loop requires proportional feedback to ensure tracking of $\theta_S[k]$. The DT equations for feedback control are as follows:

$$e_\theta[k] = \theta_c[k] - \theta[k] \quad (15)$$

$$e_\omega[k] = k_\theta e_\theta[k] + \omega_c[k] - \hat{\omega}_{fb}[k]$$

$$e_{\omega-Iu}[k] = e_{\omega-I}[k-1] + \frac{k_I T_s}{2}(e_\omega[k] + e_\omega[k-1])$$

$$e_{\omega-I}[k] = sat(e_{\omega-Iu}[k], e_{\omega-I-min}, e_{\omega-I-max})$$

$$i_{q-set} = \frac{1}{K}(k_p e_\omega[k] + e_{\omega-I}[k]).$$

In one embodiment, the integrator limits are chosen from the physical limits of the quadrature current amplifier such that $e_{\omega-I-min} = -e_{\omega-I-max} = K i_{q-max}$ in which $i_{q-max}$ is the absolute max drive current of the amplifier. In one embodiment, a quadrature current controller is approximated by a zero order hold block (ZOH) 408 such that $i_q(t) = i_{q-set}(k)$ for $t \in [kT_S, (k+1)T_S)$.

Returning to FIG. 6, in another embodiment, the motor is a stepper motor and at block 304 the two alpha-beta phase currents $i_\alpha$ and $i_\beta$ are measured using, for example, a current sensor or set at a predetermined setpoint, for example, the phase currents may be assumed based on a desired setpoint to a stepper motor current controller. A quadrature current (Q-current, $i_q$) may be calculated from the phase command currents $i_\alpha$, $i_\beta$, and the angular position $\theta$ of the rotor. In one embodiment, a Q-current setpoint may be calculated using phase current setpoints and either an estimate, $n_p\theta[k]$, of the electrical angle or a measurement of the electrical angle, $\theta_e[k]$:

$$i_{q-set}[k] = (-\sin(n_p\theta[k])i_{\alpha-set}[k] + \cos(n_p\theta[k])i_{\beta-set}[k]) \quad (16)$$

The electrical angle may be measured using, for example, hall effect sensors. In another embodiment, a Q-current may be calculated using measured phase currents and either an estimate, $n_p\theta[k]$, of the electrical angle or a measurement of the electrical angle, $\theta_e[k]$:

$$i_q[k] = (-\sin(n_p\theta[k])i_\alpha[k] + \cos(n_p\theta[k])i_\beta[k]) \quad (17)$$

The electrical angle may be measured using, for example, hall effect sensors. In another embodiment, a predetermined quadrature current setpoint may be used. In one embodiment the Q-current is converted to a PWM signal, specifically, a PWM duty cycle (for example, that is cycle proportional to the ratio of the absolute desired setpoint current to the Q-current amplifiers absolute current control range) and a direction signal which indicates the sign of the current using known methods. In another embodiment, the Q-current may be used without being converted to a PWM signal.

At block 306, a load torque is estimated. In one embodiment, the motor is a BLDC motor and the load torque may be estimated using:

$$\hat{\tau}_l[k] = K i_{q-set}[k] - B\hat{\omega}[k] - J\hat{\dot{\omega}}[k] \quad (18)$$

where $\hat{\tau}_l[k]$ is the load torque, $\hat{\omega}[k]$ is the angular velocity, $\hat{\dot{\omega}}[k]$ is the angular acceleration, K is the torque constant, B is damping coefficient of the rotor, J is moment of inertia of the rotor and $i_{q-set}$ is a desired setpoint of the Q-current (maintained by the position control system described above. In another embodiment, the motor is a stepper motor and the load torque is estimated based on the phase current setpoints using:

$$i_{q\text{-}set}[k]=(-\sin(n_p\theta[k])i_{\alpha\text{-}set}[k]+\cos(n_p\theta[k])i_{\beta\text{-}set}[k]) \quad (19)$$

$$\hat{\tau}_l[k]=Ki_{q\text{-}set}[k]-B\hat{\omega}[k]-J\hat{\dot{\omega}}[k]-K_{d4}\sin(4n_p\theta[k]) \quad (20)$$

where $\hat{\tau}_l[k]$ is the load torque, $\hat{\omega}[k]$ is the angular velocity, $\hat{\dot{\omega}}[k]$ is the angular acceleration, K is the torque constant, B is damping coefficient of the rotor, J is moment of inertia of the rotor, $i_{q\text{-}set}$ is a desired setpoint of the Q-current, $i_{\alpha\text{-}set}$ is a phase current setpoint, $i_{\beta\text{-}set}$ is a phased current setpoint, $n_p$ is the number of magnetic pole pairs of the rotor, $\theta$ is the angular position of the rotor, and $K_{d4}$ is the detent torque amplitude. In an alternative embodiment, the load torque for the stepper motor may be estimated based on the measured phase currents using:

$$i_q[k]=(-\sin(n_p\theta[k])i_\alpha[k]+\cos(n_p\theta[k])i_\beta[k]) \quad (21)$$

$$\hat{\tau}_l[k]=Ki_q[k]-B\hat{\omega}[k]-J\hat{\dot{\omega}}[k]-K_{d4}\sin(4n_p\theta[k]) \quad (22)$$

where $\hat{\tau}_l[k]$ is the load torque, $\hat{\omega}[k]$ is the angular velocity, $\hat{\dot{\omega}}[k]$ is the angular acceleration, K is the torque constant, B is damping coefficient of the rotor, J is moment of inertia of the rotor, $i_q$ is the Q-current, $i_\alpha$ is a measured phase current, $i_\beta$ is a measured phase current, $n_p$ is the number of magnetic pole pairs of the rotor, $\theta$ is the angular position of the rotor, and $K_{d4}$ is the detent torque amplitude In one embodiment, the measured angular position of the stepper motor from a rotary encoder may have a phase offset such that $\theta_m=\theta+\varphi$. By assuming that the load torque $\tau_l$ and detent torque amplitude $K_{d4}$ are both zero and the system is at steady-state, the error can be estimated by:

$$\phi = \theta_m - \frac{2\arctan\left(\frac{i_\alpha}{i_\beta} \pm \frac{\sqrt{i_\alpha^2+i_\beta^2}}{i_\beta}\right)}{n_p} \quad (23)$$

Figure 9:
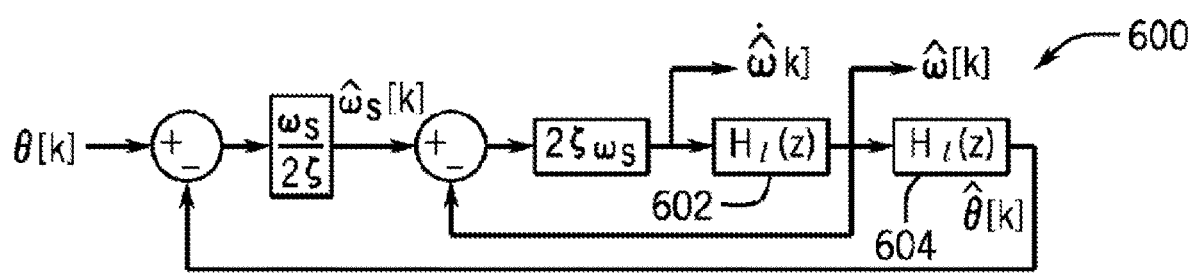
FIG. 9 illustrated a discrete time command filter in accordance with an embodiment.

For both the BLDC or stepper motor embodiments, the angular velocity $\hat{\omega}[k]$ and angular acceleration $\hat{\dot{\omega}}[k]$ may be estimated using a discrete time (DT) command filter. FIG. 9 illustrates an exemplary DT command filter for estimating angular velocity and acceleration in accordance with an embodiment. The DT command filter 600 includes two DT integrators 602, 604 which are denoted by the DT transfer function:

$$H_I(z) = \frac{Y_I(z)}{U_I(z)} = \frac{T_s}{2}\frac{z+1}{z-1} \quad (24)$$

where the DT relationship is given by equation (4). The DT command filter may be implemented to estimate angular velocity and angular acceleration for either a BLDC or stepper motor using:

$$\hat{\omega}_s[k] = \frac{\omega_n}{2\zeta}(\theta[k] - \hat{\theta}[k]), \zeta \in (0,1], \omega_n > 0 \quad (25)$$

$$\hat{\dot{\omega}}[k] = 2\zeta\omega_n(\hat{\omega}_s[k] - \hat{\omega}[k]) \quad (26)$$

$$\hat{\omega}[k] = \hat{\omega}[k-1] + \frac{T_s}{2}(\hat{\dot{\omega}}[k] + \hat{\dot{\omega}}[k-1]) \quad (27)$$

$$\hat{\theta}[k] = \hat{\theta}[k-1] + \frac{T_s}{2}(\hat{\omega}[k] + \hat{\omega}[k-1]) \quad (28)$$

The loops need to be solved for the above DT filter given by equations 26 and 27 and may be realized in the following vector form:

$$\left(I - \frac{T_s}{2}A_c\right)\begin{bmatrix}\hat{\theta}[k]\\\hat{\omega}[k]\end{bmatrix} = \left(I + \frac{T_s}{2}A_c\right)\begin{bmatrix}\hat{\theta}[k-1]\\\hat{\omega}[k-1]\end{bmatrix} + \frac{T_s}{2}B_c(\theta[k]+\theta[k-1]) \quad (29)$$

in which $$A_c = \begin{bmatrix} 0 & 1 \\ -\omega_n^2 & -2\zeta\omega_n \end{bmatrix} \text{ and } B_c = [0, \omega_n^2]^\top \quad (30)$$

Therefore, the DT filter may be implemented by:

$$\begin{bmatrix}\hat{\theta}[k]\\\hat{\omega}[k]\end{bmatrix} = \Phi_c\begin{bmatrix}\hat{\theta}[k-1]\\\hat{\omega}[k-1]\end{bmatrix} + \Gamma_c(\theta[k]+\theta[k-1]) \quad (31)$$

in which $$\Phi_c = \left(I - \frac{T_s}{2}A_c\right)^{-1}\left(I + \frac{T_s}{2}A_c\right) \quad (32)$$

and $$\Gamma_c = \left(I - \frac{T_s}{2}A_c\right)^{-1}\frac{T_s}{2}B_c. \quad (33)$$

Which allows $\hat{\dot{\omega}}[k]$ to be computed as follows $$\hat{\dot{\omega}}[k] = [-\omega_n^2 \quad -2\zeta\omega_n]\begin{bmatrix}\hat{\theta}[k]\\\hat{\omega}[k]\end{bmatrix} + \omega_n^2\theta[k] \quad (34)$$

At block 308, the estimated load torque may be used to control the motor to operate a drive mechanism and cause movement (e.g., advance, retract, rotate) of a percutaneous device in the catheter procedure system. For example, the controller 134 (shown in FIG. 4) may be configured to adjust the angular position, angular speed and acceleration of the motor based on the estimated load torque. In another embodiment, the estimated load torque may be used to determine if the motor (and the devices driven by the motor) are within an acceptable range of operation. For example, if the load torque is higher than a predetermined maximum load torque then a warning signal may be provided (e.g., on a display) or a signal may be provided from the controller to the motor to stop the motor. In one embodiment, the load torque may be displayed on a monitor (or other display) to a user of the catheter procedure system. In another embodiment, the controller 134 may provide a feedback signal to a user interface 126 (shown in FIG. 1) based on the load torque.

Computer-executable instructions for controlling a motor including determining a load torque using the motor according to the above-described method may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which can be used to store the desired instructions and which may be accessed by system 10 (shown in FIG. 1), including by internet or other computer network form of access.

This written description used examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

I claim:

1. A catheter procedure system comprising:
   a bedside system comprising a percutaneous device, at least one drive mechanism coupled to the percutaneous device and at least one motor coupled to the at least one drive mechanism, the at least one motor including at least one of a brushless DC motor or a stepper motor; and
   a workstation coupled to the bedside system, the workstation comprising:
      a user interface; and
      a controller coupled to the bedside system and the user interface, the controller programmed to:
         receive at least one parameter of the motor;
         determine a quadrature current of the motor based on the at least one parameter;
         determine a load torque on the motor based on at least the quadrature current, an angular velocity and an angular acceleration; and
         control the operation of the motor based on the load torque, wherein the operation of the motor causes the drive mechanism to move the percutaneous device,
   wherein the load torque for the brushless DC motor is determined in accordance with:

$$\hat{\tau}_l[k] = K i_{q\text{-}set}[k] - B\hat{\omega}[k] - J\hat{\dot{\omega}}[k]$$

where $\hat{\tau}_l[k]$ is the load torque, $\hat{\omega}[k]$ is the angular velocity, $\hat{\dot{\omega}}[k]$ is the angular acceleration, K is a torque constant, B is damping coefficient of the rotor, J is moment of inertia of the rotor and $i_{q\text{-}set}$ is a desired setpoint of the quadrature current, and
   wherein the load torque for the stepper motor is determined in accordance with:

$$i_q[k] = (-\sin(n_p\theta[k])i_\alpha[k] + \cos(n_p\theta[k])i_\beta[k])$$

$$\hat{\tau}_l[k] = K i_q[k] - B\hat{\omega}[k] - J\hat{\dot{\omega}}[k] - K_{d4}\sin(4n_p\theta[k])$$

where $i_q$ is the quadrature current, $i_\alpha$ is a measured phase current, $i_\beta$ is a measured phase current, $n_p$ is a number of magnetic pole pairs of the rotor, $\theta$ is the angular position of the rotor, and $K_{d4}$ is a detent torque amplitude.

2. A catheter procedure system according to claim 1, wherein the motor is a brushless DC motor.

3. A catheter procedure system according to claim 2, further comprising controlling the quadrature current to maintain the quadrature current at a predetermined setpoint.

4. A catheter procedure system according to claim 3, further comprising generating a pulse width modulated signal based on the quadrature current.

5. A catheter procedure system according to claim 1, wherein the motor is a stepper motor.

6. A catheter procedure system according to claim 1, wherein the at least one parameter is an angular position of the motor.

7. A catheter procedure system according to claim 1, wherein the at least one parameter is a phase current of the motor.

8. A catheter procedure system according to claim 1, wherein the angular velocity and angular acceleration are estimated using a discrete time command filter using two discrete time integrators with a saturation function.

9. A catheter procedure system according to claim 1, wherein determining a quadrature current comprises measuring the quadrature current.

10. A catheter procedure system according to claim 1, wherein the operation of the motor causes the drive mechanism to cause the percutaneous device to advance.

11. A catheter procedure system according to claim 1, wherein the operation of the motor causes the drive mechanism to cause the percutaneous device to retract.

12. A catheter procedure system according to claim 1, wherein the operation of the motor causes the drive mechanism to cause the percutaneous device to rotate.

13. A catheter procedure system according to claim 1, wherein the controller provides a feedback signal to the user interface based on the load torque.

14. A catheter procedure system according to claim 1, wherein workstation further comprises a monitor coupled to the user interface and the controller, wherein the load torque is displayed on the monitor.

15. A method for controlling a motor in a catheter procedure system, the method comprising:
   receiving at least one parameter of the motor;
   determining a quadrature current of the motor based on at least the at least one parameter;
   determining a load torque on the motor based on at least the quadrature current, an angular velocity and an angular acceleration; and
   controlling the operation of the motor based on the load torque, wherein the operation of the motor causes the drive mechanism to move the percutaneous device, wherein the load torque for a brushless DC motor is determined in accordance with:

$$\hat{\tau}_l[k]=Ki_{q\text{-}set}[k]-B\hat{\omega}[k]-J\hat{\dot{\omega}}[k]$$

where $\tau_l[k]$ is the load torque, $\hat{\omega}[k]$ is the angular velocity, $\hat{\dot{\omega}}[k]$ is the angular acceleration, K is a torque constant, B is damping coefficient of the rotor, J is moment of inertia of the rotor and $i_{q\text{-}set}$ is a desired setpoint of the quadrature current, and wherein the load torque for a stepper motor is determined in accordance with:

$$i_q[k]=(-\sin(n_p\theta[k])i_\alpha[k]+\cos(n_p\theta[k])i_\beta[k])$$

$$\hat{\tau}_l[k]=Ki_q[k]-B\hat{\omega}[k]-J\hat{\dot{\omega}}[k]-K_{d4}\sin(4n_p\theta[k])$$

where $i_q$ is the quadrature current, $i_\alpha$ is a measured phase current, $i_\beta$ is a measured phase current, $n_p$ is a number of magnetic pole pairs of the rotor, $\theta$ is the angular position of the rotor, and $K_{d4}$ is a detent torque amplitude.

16. A method according to claim 15, wherein the motor is a brushless DC motor.

17. A method according to claim 16, further comprising controlling the quadrature current to maintain the quadrature current at a predetermined setpoint.

18. A method according to claim 17, further comprising generating a pulse width modulated signal based on the quadrature current.

19. A method according to claim 15, wherein the motor is a stepper motor.

20. A method according to claim 15, wherein the at least one parameter is an angular position of the motor.

21. A method according to claim 15, wherein the at least one parameter is a phase current of the motor.

22. A method according to claim 15, wherein the angular velocity and angular acceleration are estimated using a discrete time command filter.

23. A method according to claim 15, wherein determining a quadrature current comprises measuring the quadrature current.

24. A method according to claim 15, further comprising displaying the load torque on a monitor.

* * * * *